(12) United States Patent
Hwang et al.

(10) Patent No.: US 7,763,429 B2
(45) Date of Patent: Jul. 27, 2010

(54) COMPOUND CONTAINING FARNESYL DIPHOSPHATE FOR MODULATING TRPV3 FUNCTION AND USE THEREOF

(75) Inventors: Sun Wook Hwang, Seoul (KR); Sang-Soo Bang, Gyeonggi-do (KR)

(73) Assignee: Korea University Industry and Academic Collaboration Foundation, Seoul (KR)

( * ) Notice: Subject to any disclaimer, the term of this patent is extended or adjusted under 35 U.S.C. 154(b) by 0 days.

(21) Appl. No.: 12/388,278

(22) Filed: Feb. 18, 2009

(65) Prior Publication Data

US 2010/0136533 A1 Jun. 3, 2010

(30) Foreign Application Priority Data

Dec. 2, 2008 (KR) .................. 10-2008-0121093

(51) Int. Cl.
*C12Q 1/68* (2006.01)
*G01N 33/53* (2006.01)
*G01N 33/566* (2006.01)

(52) U.S. Cl. .................. 435/6; 435/7.1; 435/7.2; 436/501

(58) Field of Classification Search .................. None
See application file for complete search history.

(56) References Cited

U.S. PATENT DOCUMENTS

| 7,429,673 | B2 | 9/2008 | Morazzoni et al. |
| 2006/0270688 | A1 | 11/2006 | Chong et al. |
| 2007/0179164 | A1 | 8/2007 | Chong et al. |
| 2007/0213321 | A1 | 9/2007 | Chong et al. |
| 2008/0146611 | A1 | 6/2008 | Moran et al. |

FOREIGN PATENT DOCUMENTS

| WO | WO 2006/122156 | 11/2006 |
| WO | WO 2007/056124 | 5/2007 |
| WO | WO 2008/033564 | 3/2008 |
| WO | WO 2008/060626 | 5/2008 |
| WO | WO 2008/140750 | 11/2008 |

OTHER PUBLICATIONS

Gu, et al. "2-Aminoethoxydiphenyl borate stimulates pulmonary C neurons via the activation of TRPV channels"; *Am. J. Physiol Lung Cell Mol. Physiol.* (2005) 288;L932-L941.
Moqrich, A. et al. "Impaired thermosensation in Mice Lacking TRPV3, a Heat and Camphor Sensore in the Skin"; *Science* (Mar. 4, 2005) 307;1468-1472.
Vogt-Eisele, AK et al. "Monotderpenoid agonists of TRPV3", *Brit.J. Pharmacol.* (2007) 151:530-540.

*Primary Examiner*—Christine J Saoud
*Assistant Examiner*—Jon M Lockard
(74) *Attorney, Agent, or Firm*—Greenlee Winner and Sullivan PC

(57) ABSTRACT

The present invention relates to a method for activating TRPV3 (transient receptor potential vanilloid 3) using FPP (farnesyl diphosphate) and a method for screening a TRPV3 activity inhibitor. FPP of the present invention has TRPV3 specific activity and therefore it can be effectively used for the study on TRPV3 mechanism and functions and for the development of a TRPV3 based pain reliever.

6 Claims, 6 Drawing Sheets

SEQUENCE LISTING

```
<160> NUMBER OF SEQ ID NOS: 6

<210> SEQ ID NO 1
<211> LENGTH: 2847
<212> TYPE: DNA
<213> ORGANISM: Rattus norvegicus

<400> SEQUENCE: 1
cagctccaag gcacttgctc catttggggt gtgcctgcac ctagctggtt gcaaattggg      60
ccacagagga tctggaaagg atggaacaac gggctagctt agactcagag gagtctgagt     120
ccccacccca agagaactcc tgcctggacc ctccagacag agaccctaac tgcaagccac     180
ctccagtcaa gccccacatc ttcactacca ggagtcgtac ccggcttttt gggaagggtg     240
actcggagga ggcctctccc ctggactgcc cttatgagga aggcgggctg gcttcctgcc     300
ctatcatcac tgtcagctct gttctaacta tccagaggcc tggggatgga cctgccagtg     360
tcaggccgtc atcccaggac tccgtctccg ctggtgagaa gccccgagg ctctatgatc      420 gcaggagcat cttcgatgct gtggctcaga gtaactgcca ggagctggag agcctgctgc     480
ccttcctgca gaggagcaag aagcgcctga ctgacagcga gttcaaagac ccagagacag     540
gaaagacctg tctgctaaaa gccatgctca atctgcacaa tgggcagaat gacaccatcg     600
ctctgctcct ggacgttgcc cggaagacag acagcctgaa gcagtttgtc aatgccagct     660
acacagacag ctactacaag ggccagacag cactgcacat tgccattgaa cggcggaaca     720
tgacgctggt gaccctcttg gtggagaatg gagcagatgt ccaggctgcg gctaacgggg     780
acttcttcaa gaaaaccaaa gggaggcctg gcttctactt tggtgagctg cccctgtccc     840
```

```
tggctgcgtg caccaaccag ctggccattg tgaagttcct gctgcagaac tcctggcagc    900
ctgcagacat cagcgcccgg gactcagtgg gcaacacggt gcttcatgcc ctggtggagg    960
tggcagataa cacagttgac aacaccaagt tcgtgacaag catgtacaac agagatcttga  1020
tcctgggggc caaactccac cccacgctga agctggaaga gatcaccaac aggaaggggc   1080
tcacgccact ggctctggct gctagcagtg ggaagatcgg ggtcttggcc tacattctcc   1140
agagggagat ccatgaaccc gagtgccgac acctatccag gaagttcacc gaatgggcct   1200
atgggccagt gcactcctcc ctttatgacc tgtcctgcat tgacacctgt gaaaagaact   1260
cggttctgga ggtgatcgct tacagcagca gtgagacccc taaccgtcat gacatgcttc   1320
tcgtggaacc cttgaaccga ctcctacagg acaagtggga cagatttgtc aagcgcatct   1380
tctacttcaa cttcttcgtc tactgcttgt atatgatcat cttcaccgcg gctgcctact   1440
atcggcctgt ggaaggcttg ccccctata agctgaaaaa caccgttggg gactatttcc    1500
gagtcaccgg agagatcttg tctgtgtcag gaggagtcta cttcttcttc cgagggattc   1560
aatatttcct gcagaggcga ccatccctca gagtttgtt tgtggacagc tacagtgaga   1620
tactttttctt tgtacagtcg ctgttcatgc tggtgtctgt ggtactgtac ttcagccaac   1680
gcaaggagta tgtggcttcc atggtgttct ccctggccat gggctggacc aacatgctct   1740
actatacccg aggattccag cagatgggca tctatgctgt catgattgag aagatgatcc   1800
tcagagacct gtgccggttt atgttcgtct acctcgtgtt cttgtttgga ttttccacag   1860
ctgtggtgac actgattgag gatgggaaga ataactctct gcctatggag tccacaccac   1920
acaagtgccg ggggtctgcc tgcaagccag gtaactctta caacagcctg tattccacat   1980
gtctggagct gttcaagttc accatcggca tgggcgacct ggagttcact gagaactacg   2040
acttcaaggc tgtcttcatc atcctgttac tggcctatgt gattctcacc tacatccttc   2100
tgctcaacat gctcattgct ctcatgggtg agaccgtcaa caagattgca caagagagca   2160
agaacatctg gaagctgcag agagccatca ccatcctgga tacagagaag agcttcctga   2220
agtgcatgag gaaggccttc cgctctggca agctgctgca ggtggggttc actcctgacg   2280
gcaaggatga ctaccggtgg tgtttcaggg tggacgaggt aaactggact acctggaaca   2340
ccaatgtggg tatcatcaac gaggacccag gcaactgtga gggcgtcaag cgcaccctga   2400
gcttctccct gaggtcaggc cgagtttcag ggagaaactg aagaactttt gccctggttc   2460
cccttctgag ggatgcaagc actcgagata gacatgccac ccagcaggaa gaagttcaac   2520
tgaagcatta tacgggatcc cttaagccag aggatgctga ggttttcaag gattccatgg   2580
tcccagggga gaaataatgg acactatgca gggatcaatg cggggtcttt gggtggtctg   2640
cttagggaac cagcagggtt gacgttatct gggtccactc tgtgcctgcc taggcacatt   2700
cctaggactt cggcgggcct gctgtgggaa ctgggaggtg tgtgggaatt gagatgtgta   2760
tccaaccatg atctccaaac atttggcttt caactcttta tggactttat taaacagagt   2820
gaatggcaaa tctctacttg gacacat                                        2847

<210> SEQ ID NO 2
<211> LENGTH: 2768
<212> TYPE: DNA
<213> ORGANISM: Rattus norvegicus

<400> SEQUENCE: 2
ctgctctgtc cactgtgtga gacgaacagg tggagggtgg acgacgcaga gaaagctcgg     60
agcgggccgc ggaggttccc acagccccat tactgtcagc gttgagccgc accctccgg    120
```

-continued

```
gccgcacttc ctctctcagt ccccgctgcc ggagagcccc gctaggctcg gtgatcctag      180
cctgcagttt gccgccgcta caccttggct tcagcctgcg ggcccctctc catcaccttc      240
tccaggtccc agccaggcct gcccctgcgg tatgagagag gaaccttaac atctccatct      300
ctacagaggt ttcagctgta aggagcatcc tcctctctca ggatgacttc agcctccagc      360
cccccagctt tcaggctgga gacttccgat ggagatgaag agggcaatgc tgaggtgaac      420
aaggggaagc aggaaccgcc ccccatggag tcaccattcc agagggagga ccggaattcc      480
tcccctcaga tcaaagtgaa cctcaacttc ataaagagac ctcctaaaaa cacttctgct      540
cccagccagc aggagccaga tcggtttgac cgtgaccgac tcttcagtgt ggtctcccgg      600
ggtgtccccg aggaactgac tggactgcta gaatacctgc gctggaacag caagtacctc      660
actgactctg catacacaga aggctccact ggaaagacgt gcctgatgaa ggctgtgctg      720
aaccttcagg atggggtcaa tgcctgcatc atgccgctgc tgcagattga caaggattcc      780
ggcaatccca gcccctcgt caatgcccag tgcatcgatg agttctacca aggccacagt      840
gcgctgcaca tcgccataga gaagaggagc ctgcagtgcg tgaagctgct ggtagagaat      900
ggagcggatg ttcacctccg agcctgtggc cgcttcttcc aaaagcacca aggaacttgt      960
ttctattttg gagagctacc tctttctctg gctgcgtgca ccaagcagtg ggatgtggtg     1020
acctacctcc tggagaaccc acaccagccg gccagcctgg aggccaccga ctccctgggc     1080
aacacagtcc tgcatgctct ggtaatgatt gcagataact cgcctgagaa cagtgccctg     1140
gtgatccaca tgtacgacgg gcttctacaa atgggggcgc gcctctgccc cactgtgcag     1200
cttgaggaaa tctccaacca ccaaggcctc acacccctga actagccgc caaggaaggc     1260 aaaatcgaga ttttcaggca cattctgcag cgggaattct caggaccgta ccagcccctt     1320
tcccgaaagt ttactgagtg gtgttacggt cctgtgcggg tatcgctgta cgacctgtcc     1380
tctgtggaca gctgggaaaa gaactcggtg ctggagatca tcgcttttca ttgcaagagc     1440
ccgaaccggc accgcatggt ggttttagaa ccactgaaca agcttctgca ggagaaatgg     1500
gatcggctcg tctcaagatt cttcttcaac ttcgcctgct acttggtcta catgttcatc     1560
ttcaccgtcg ttgcctacca ccagccttcc ctggatcagc cagccatccc ctcatcaaaa     1620
gcgacttttg gggaatccat gctgctgctg gccacattc tgatcctgct tgggggtatt      1680
tacctcttac tgggccagct gtggtacttt tggcggcggc gcctgttcat ctggatctca     1740
ttcatggaca gctactttga aatcctcttt ctccttcagg ctctgctcac agtgctgtcc     1800
caggtgctgc gcttcatgga gactgaatgg tacctacccc tgctagtgtt atccctagtg     1860
ctgggctggc tgaacctgct ttactacaca cggggctttc agcacacagg catctacagt     1920
gtcatgatcc agaaggtcat ccttcgagac ctgctccgtt tcctgctggt ctacctggtc     1980
ttccttttcg gctttgctgt agccctagta agcttgagca gagaggcccg aagtcccaaa     2040
gcccctgaag ataacaactc cacagtgacg gaacagccca cggtgggcca ggaggaggag     2100
ccagctccat atcggagcat tctggatgcc tccctagagc tgttcaagtt caccattggt     2160 atggggagc tggctttcca ggaacagctg cgttttcgtg gggtggtcct gctgttgctg     2220
ttggcctacg tccttctcac ctacgtcctg ctgctcaaca tgctcattgc tctcatgagc     2280
gaaactgtca accacgttgc tgacaacagc tggagcatct ggaagttgca gaaagccatc     2340
tctgtcttgg agatggagaa tggttactgg tggtgccgga ggaagaaaca tcgtgaaggg     2400
aggctgctga aagtcggcac caggggggat ggtacccctg atgagcgctg gtgcttcagg     2460
```

```
gtggaggaag taaattgggt tgcttgggag aagactcttc ccaccttatc tgaggatcca    2520
tcagggccag gcatcactgg taataaaaag aacccaacct ctaaaccggg aagaacagt     2580 gcctcagagg aagaccatct gccccttcag gtcctccagt cccccctgatg cccagatgc    2640 agcagcaggc tggcaggatg gagtagggaa tcttcccagc cacaccagag gctactgagt    2700
tttggtggaa atataaatat tttttttgcat aaccaaaaaa aaaaaaaaaa aaaaaaaaa    2760 aaaaaagg                                                              2768

<210> SEQ ID NO 3
<211> LENGTH: 2440
<212> TYPE: DNA
<213> ORGANISM: Mus musculus

<400> SEQUENCE: 3
gatctcaagg caaggactgc caccaccatc tggaacctgc agcatatgc cttaggctcc       60 agcaatgaat gcccactcca aggagatggt gcccctcatg ggcaaaagaa ccacggcacc     120
tggcgggaac cctgttgtac tgacagagaa gaggccagca gatctcaccc ccaccaagaa    180
gagtgcacac ttcttcctgg agatagaagg atttgagccc aaccccacgg tcaccaagac    240
ctctccaccc atcttctcca agccgatgga ctccaacatc cggcagtgcc tctctggcaa    300
ctgtgatgac atggactctc cccagtctcc tcaggatgat gtgacagaga ccccatccaa    360
tcccaacagt ccgagcgcaa acctggccaa ggaagaacag aggcagaaga agaagcgact    420
gaagaagcgc atcttcgcgg ctgtgtccga gggctgcgtg gaggagctgc gggaactcct    480
acaggatctg caggacctct gcaggaggcg ccgcggcctg gatgtgcctg acttcctcat    540
gcacaagctg acagcctcag acaccgggaa gacctgcctg atgaaggctt tgctcaacat    600
caatcccaac accaaagaga tcgtgcggat tctgcttgcc ttcgctgagg agaacgacat    660
cctggacagg ttcatcaacg ctgagtacac ggaagaggcc tatgaagggc agacagcgct    720
gaacatcgcc atcgagcggc gccagggaga catcacagca gtgcttatag cagcgggtgc    780
tgacgtcaat gctcacgcca aggggggtctt cttcaacccc aaatccagc atgaaggctt    840 ctatttttggc gagacacccc tggctttggc agcgtgtact aaccagcctg agattgtgca    900
gctgctgatg gagaatgagc agacagacat cacttcccag gattcccggg gaaacaacat    960
cctgcacgcg ctggtgacag tggctgagga cttcaagact cagaatgact tcgttaagcg   1020
catgtatgac atgatcctgc tgaggagtgg caactgggag ctggagacca tgcgcaacaa   1080
cgatgggctc acaccactgc agctggctgc caagatgggc aaggctgaga tcctgaagta   1140
catcctcagc cgcgagatca aggagaagcc tctccggagc ttgtccagga agttcacgga   1200
ctgggcgtat gggcctgtgt catcctcact ctatgacctc accaatgtag acacaacgac   1260
ggataactct gtgctggaaa tcatcgtcta caaccccaac attgataacc gacatgagat   1320
gctgaccctg gagcctctgc atacgctgct acacacgaaa tggaagaaat ttgccaagta   1380
catgttcttc ttgtccttct gcttctattt cttctacaac atcaccctga cccttgtctc   1440
ttactaccgt cctcgggaag atgaggatct cccacacccc ttggccctga cacacaaaat   1500
gagttggctt cagctcctag gaaggatgtt tgtcctcatc tgggccacat gcatctctgt   1560
gaaagaaggc attgccattt tcctgctgag accctccgat cttcagtcca tcctgtcaga   1620
tgcctggttt cactttgtct tttttgtcca agctgtactt gtgatactgt ctgtattctt   1680
gtacttgttt gcctacaaag aatacctcgc ctgcctcgtg ctggcatgg ccctgggctg   1740 ggcgaacatg ctctactaca cgagaggctt ccagtctatg ggcatgtaca gcgtcatgat   1800
```

-continued

| | |
|---|---|
| ccagaaggtc attttgcatg atgtcctcaa gttcttgttt gtttacatcc tgttcttact | 1860 |
| tggatttgga gtagcgctgg cctcactgat tgagaagtgc tccaaggaca aaaaggactg | 1920 |
| cagttcctat ggcagcttca gcgacgcggt gctggagctc ttcaagctca cataggcct | 1980 |
| gggcgacctg aacatccagc agaactccac ctaccccatc ctctttctct tcctactcat | 2040 |
| cacctatgtc atcctcacct tcgtcctcct cctcaacatg ctcatcgccc tgatggggga | 2100 |
| gacggtggag aacgtctcca agaaagtga gcggatctgg cgcttgcaga gagccaggac | 2160 |
| catcttggag tttgagaaaa tgttaccaga atggctgaga agcagattcc gcatgggcga | 2220 |
| gctgtgcaaa gtagcagatg aggacttccg gctgtgtctg cggatcaacg aggtgaagtg | 2280 |
| gacggaatgg aaaacacacg tgtccttcct taatgaagac ccgggaccca taagacggac | 2340 |
| agcagattta acaagattc aagattcttc caggagcaat agcaaaacca ccctctatgc | 2400 |
| gtttgatgaa ttagatgaat cccagaaac gtcggtgtag | 2440 |

<210> SEQ ID NO 4
<211> LENGTH: 3211
<212> TYPE: DNA
<213> ORGANISM: Rattus norvegicus

<400> SEQUENCE: 4

| | |
|---|---|
| gggaggagga cgcggcggga tcaggaagcg gctgcgctgc gcccgcgtcc caagcaggcc | 60 |
| gagaagtcca acagatctg ctcagggtcc agtatggcag atcctggtga tggccccgt | 120 |
| gcagcgcctg gggatgtggc tgagccccct ggagacgaga gtggcacttc tggtggggag | 180 |
| gccttccccc tctcttccct ggccaacctg tttgagggag aggaaggctc ctcttctctt | 240 |
| tcaccagtgg atgctagccg ccctgctggc cccggggatg gacgtccaaa cctgcgtatg | 300 |
| aagttccagg gcgctttccg caaggggtt cccaacccca ttgacctgct ggagtccacc | 360 |
| ctgtatgagt cctcagtagt gcctgggccc aagaaagcgc ccatggattc gttgttcgac | 420 |
| tatggcactt accggcacca ccccagtgac aacaagagat ggaggaggaa ggtcgtagag | 480 |
| aagcagccac agagccccaa agctcccgcc cccagccac ccccatcct caaagtcttc | 540 |
| aaccggccca tcctcttga catcgtgtcc cggggctcca ctgccgacct ggacggactg | 600 |
| ctctcctact tgctgaccca caagaagcgc ctgactgatg aggagttccg ggaaccatcc | 660 |
| acagggaaga cctgcctgcc caaggcactt ctgaacttaa gcaatggccg aaacgacacc | 720 |
| atcccagtgt tgctggacat tgcggaacgc acgggcaaca tgcggagtt catcaactcg | 780 |
| cccttcagag acatctacta ccgagggcag acggcactgc acatcgccat tgaacggcgc | 840 |
| tgcaagcatt acgtggagct cctggtggcc caggagccg atgtgcacgc gcaggcccga | 900 |
| gggcggttct tccagcccaa ggatgagggt ggctacttct actttgggga gctgcccttg | 960 |
| tccttggcag cctgcaccaa ccagccgcac atcgtcaact acctgacaga gaaccctcac | 1020 |
| aagaaagccg atatgaggcg acaggactcc agaggcaaca cggtgctcca cgcgctggtg | 1080 |
| gccatcgctg acaacacccg agagaacacc aagtttgtca ccaagatgta tgacctgttg | 1140 |
| cttctcaagt gctcccgcct cttcccagac agcaacctgg agactgtgct aacaatgac | 1200 |
| ggtctttcgc ccctcatgat ggctgccaag actggcaaga tcgggtcttt cagcacatc | 1260 |
| atccgacggg aggtgacaga tgaggacaca cggcacctgt ctcgcaagtt caaggactgg | 1320 |
| gcctacgggc ctgtgtattc ttctctctac gacctctcct ccctggatac gtgcggggag | 1380 |
| gaagtgtccg tgctggagat cctggtttac aacagcaaga tcgagaaccg ccatgagatg | 1440 |

| | |
|---|---|
| ctggctgtgg agcccattaa cgaactgctg agggacaagt ggcgtaagtt cggggccgtg | 1500 |
| tccttctaca tcaacgttgt ctcctatctg tgtgccatgg tcatcttcac cctcacagcc | 1560 |
| tactatcagc cactggaggg cacgccaccc taccottacc gtaccacggt ggactacctg | 1620 |
| aggctggctg gtgaggtcat cacgctcctc acaggagtcc tgttcttctt taccagtatc | 1680 |
| aaagacttgt tcatgaagaa atgccctgga gtgaattctc tcttcgtcga tggctccttc | 1740 |
| cagttgctct acttcatcta tcagtgctg gtggttgtgt ctgcggcgct ctacctggca | 1800 |
| gggatcgagg cctatctggc tgtgatggtc tttgccctgg tcctgggctg gatgaatgcc | 1860 |
| ctttacttca cccgtgggct gaagctgaca gggacctaca gcatcatgat tcagaagatc | 1920 |
| ctcttcaaag atctcttccg ctttctgctg gtctacctgc tttttatgat tggctatgcc | 1980 |
| tcagctctgg tcaccctcct gaatccgtgc accaacatga aggtctgtaa cgaggaccag | 2040 |
| agcaactgca cggtgccctc ataccccgcg tgccgggaca gcgagaccct cagcgccttc | 2100 |
| ctactggacc tcttcaagct caccatcggc atgggcgacc tggagatgct gagcagcgct | 2160 |
| aagtaccccg tggtcttcat tctcctgctg gttacctaca tcatcctcac cttcgtgctc | 2220 |
| ctgctgaaca tgctcatcgc cctcatgggt gagaccgtgg ccaggtgtc caaggagagc | 2280 |
| aagcacatct ggaagctgca gtgggccacc accatcctgg acatcgagcg ctccttccct | 2340 |
| gtgttcctga ggaaggcctt ccgctccgga gagatggtga cagtgggcaa gagctcggat | 2400 |
| ggcactccag accgcaggtg gtgcttcagg gtggacgagg tgaactggtc tcactggaac | 2460 |
| cagaacctgg gcatcattaa cgaggacccc ggcaagagcg agatctacca gtactatggc | 2520 |
| ttctccccata ccatggggcg cctccgcagg gatcgctggt cctcagtggt gccccgcgtg | 2580 |
| gtggagctga acaagaactc aggcacagat gaagtggtgg tccccctgga taacctaggg | 2640 |
| aaccccaact gtgacggcca ccagcaaggt tatgctccca gtggagggc ggaggacgca | 2700 |
| ccactgtagg ggccatgcca gggctggggt caatggccca ggcttggccc ttgctcccac | 2760 |
| ctacatttca gcatctgtcc tgtgtcttcc cacacccaca cgtgacctcg gaggtgaggg | 2820 |
| cctctgtgga gactctgggg aggccccagg accctctggt ccccacaaag acttttgctc | 2880 |
| ttatttctac tcctccccac atgggggacg gggctcctgg ccacctgtct cactcccatg | 2940 |
| gagtcaccta agccagctca gggcccctcc actcacaggg ctcaggcccc tgtccctctt | 3000 |
| gtgcactatt tattgctctc ctcaggaaaa tgacatcaca ggagtctacc tgcagctgga | 3060 |
| acctggccag ggctgaggct catgcaggga cactgcagcc ctgacccgct gcagatctga | 3120 |
| cctgctgcag cccgggctag ggtgggtctt ctgtactttg tagagatcgg ggctgttggt | 3180 |
| gctcaataaa tgtttgttta ttctcggtgg a | 3211 |

<210> SEQ ID NO 5
<211> LENGTH: 3869
<212> TYPE: DNA
<213> ORGANISM: Mus musculus

<400> SEQUENCE: 5

| | |
|---|---|
| tcctcccctcc tccagtgagc taagagacaa gcaggctctt tgaggagaga gaagctcttg | 60 |
| gctgattgag cagctccacg tcctggctgt cccggagctt gatacataga aaagactgac | 120 |
| ctcagataca cagagatcct tctgcttctg tctcccaagt gctgggatca caggcaagat | 180 |
| gtccttcgag ggagccaggc tcagcatgag gagccgcaga aatggtacta tgggcagcac | 240 |
| ccggaccctg tactccagtg tatctcggag cacagacgtg tcctacagtg acagtgattt | 300 |
| ggtgaatttt attcaggcaa attttaaaaa acgagaatgt gtcttcttta ccagagactc | 360 |

| | | | | | |
|---|---|---|---|---|---|
| caaggccatg | gagaacatat | gcaagtgtgg | ttatgcccag | agccagcaca | tcgaaggcac | 420 |
| ccagatcaac | caaaatgaga | agtggaacta | caaaaaacat | accaaggagt | ttccaacaga | 480 |
| cgccttcggg | gacattcagt | ttgagactct | ggggaagaaa | ggcaagtact | tacgcttgtc | 540 |
| ctgtgacacc | gactctgaaa | ctctctacga | actgctgacc | cagcactggc | acctcaaaac | 600 |
| acccaacctg | gtcatttcag | tgacgggtgg | agccaaaaac | tttgctttga | agccacgcat | 660 |
| gcgcaagatc | ttcagcaggc | tgatttacat | cgcacagtct | aaaggtgcgt | ggattctcac | 720 |
| tggaggcact | cactacggcc | tgatgaagta | cataggcgag | gtggtgagag | acaacaccat | 780 |
| cagcaggaac | tcagaagaga | acatcgtggc | cattggcatc | gcagcatggg | gcatggtctc | 840 |
| caacagggac | accctcatca | ggagctgtga | tgatgaggga | cattttttcag | ctcaatacat | 900 |
| catggatgac | tttaccagag | accctctata | catcctggac | aacaaccata | cccacctgct | 960 |
| gcttgtggca | acggttgtc | atggacaccc | cacagtggaa | gccaagctcc | ggaatcagct | 1020 |
| ggaaaagtac | atctctgagc | gcaccagtca | agattccaac | tatggtggta | agatccccat | 1080 |
| cgtgtgtttt | gcccaaggag | gtggaagaga | gactctaaaa | gccatcaaca | cctctgtcaa | 1140 |
| aagcaagatc | ccttgtgtgg | tggtggaagg | ctcggggcag | attgctgatg | tgatcgccag | 1200 |
| cctggtggag | gtggaggatg | ttttaacctc | ttccatggtc | aaagagaagc | tggtacgctt | 1260 |
| tttaccacgc | actgtgtccc | ggctgcctga | agaggaaatt | gagagctgga | tcaaatggct | 1320 |
| caaagaaatt | cttgagagtt | ctcacctact | cacagtaatt | aagatggaag | aggctggaga | 1380 |
| tgagattgtg | agcaacgcca | tttcctatgc | gctgtacaaa | gccttcagca | ctaatgagca | 1440 |
| agacaaggac | aactgaatg | gacagctgaa | gcttctgctg | gagtggaacc | agttggacct | 1500 |
| tgccagtgat | gagatcttca | ccaatgatcg | ccgctgggag | tctgccgacc | ttcaggaggt | 1560 |
| catgttcacg | gctctcataa | aggacagacc | caagtttgtc | cgcctctttc | tggagaatgg | 1620 |
| cctgaatctg | cagaagttc | tcaccaatga | agtcctcaca | gagctcttct | ccacccactt | 1680 |
| cagcacccta | gtgtaccgga | atctgcagat | cgccaagaac | tcctacaatg | acgcactcct | 1740 |
| cacctttgtc | tggaagttgg | tggcaaactt | ccgtcgaagc | ttctggaaag | aggacagaag | 1800 |
| cagcagggag | gacttggatg | tggaactcca | tgatgcatct | ctcaccaccc | ggcacccgct | 1860 |
| gcaagctctc | ttcatctggg | ccattcttca | gaacaagaag | gaactctcca | aggtcatttg | 1920 |
| ggagcagacc | aaaggctgta | ctctggcagc | cttgggggcc | agcaagcttc | tgaagaccct | 1980 |
| ggccaaagtt | aagaatgata | tcaacgctgc | tggggaatcg | gaggaactgg | ccaatgaata | 2040 |
| tgagacccga | gcagtggagt | tgttcaccga | gtgttacagc | aatgatgaag | acttggcaga | 2100 |
| acagctactg | gtctactcct | gcgaagcctg | ggtgggagc | aactgtctgg | agctggcagt | 2160 |
| ggaggctaca | gatcagcatt | tcatcgctca | gcctgggtc | cagaatttcc | tttctaagca | 2220 |
| atggtatgga | gagatttccc | gagacacgaa | gaactggaag | attatcctgt | gtctattcat | 2280 |
| catcccctta | gtgggctgtg | gcctcgtatc | atttaggaag | aaacccattg | acaagcacaa | 2340 |
| gaagctgctg | tggtactatg | tggccttctt | cacgtcgccc | ttcgtggtct | tctcctggaa | 2400 |
| cgtggtcttc | tacatcgcct | tcctcctgct | gtttgcctat | gtgctgctca | tggacttcca | 2460 |
| ctcagtgcca | cacaccccg | agctgatcct | ctacgccctg | gtcttcgtcc | tcttctgtga | 2520 |
| tgaagtgagg | cagtggtaca | tgaacggagt | gaattatttc | accgacctat | ggaacgttat | 2580 |
| ggacaccctg | ggactcttct | acttcatagc | gggtattgta | ttccggctcc | actcttctaa | 2640 |
| taaaagctcg | ttgtactctg | ggcgcgtcat | tttctgtctg | gattacatta | tattcacgct | 2700 |

```
aaggctcatc cacattttca ccgtcagcag gaacttggga cccaagatta taatgctgca    2760
gcggatgctg atcgacgttt tcttcttcct gttcctcttt gctgtgtgga tggtggcctt    2820
tggcgtggcc agacagggga tcctaaggca aaatgaacag cgctggagat ggatcttccg    2880
ctctgtcatc tatgagccct acctggccat gtttggccag gttcccagtg acgtggatag    2940
taccacatat gacttctccc actgtacctt ctcgggaaat gagtccaagc cactgtgtgt    3000
ggagctggat gagcacaacc tgcccgctt ccctgagtgg atcaccattc cgctggtgtg    3060
catctacatg ctctccacca atatccttct ggtcaacctc ctggtcgcca tgtttggcta    3120
cacggtaggc attgtacagg agaacaacga ccaggtctgg aaattccagc ggtacttcct    3180
ggtgcaggag tactgcaacc gcctaaacat ccccttcccc ttcgttgtct tcgcttattt    3240
ctacatggtg gtgaagaagt gtttcaaatg ctgctgtaaa gagaagaata tggagtctaa    3300
tgcctgctgt ttcagaaatg aggacaatga gactttggcg tgggagggtg tcatgaagga    3360
gaattacctt gtcaagatca acacgaaagc caacgacaac tcagaggaga tgaggcatcg    3420
gtttagacaa ctggactcaa agcttaacga cctcaaaagt cttctgaaag agattgctaa    3480
taacatcaag taaggctggc gatgcttgtg gggagaaacc aaatcacaat gaggtcacag    3540
caaccacctg gatgtggagg ctcatgggac actgatggac agtactgcta atgacttcta    3600
aaggagacat tttcaggtcc ctgagcacag ggtggatgac tcttagtcac cctcaagggc    3660
ataggtcagg gagcaaagtg tacagaggac tttacacctg aagagggtg caaaggacca    3720 tgttcttctg tgaaggtgcc tgtgttttct gcatctcaga gccttgtcct gatgctgagg    3780
gattaagtgt tgacactcct ttcccacgac tgtgactctg gccctgattt tatacttata    3840
ctgcaaaaaa aaaaaaaaaa aaaaaaaaa                                      3869
```

`<210>` SEQ ID NO 6
`<211>` LENGTH: 4263
`<212>` TYPE: DNA
`<213>` ORGANISM: Mus musculus

`<400>` SEQUENCE: 6

```
gcgccagccg gcgtccaggt ggagtcaatg aagcgcggct tgaggaggat tctgctcccg     60
gaggaaagga aggaggtcca gggcgttgtc tatcgcggcg tcggggaaga catggactgc    120
tccaaggaat cctttaaggt ggacattgaa ggagatatgt gtagattaga agacttcatc    180
aagaaccgaa gaaaactaag caaatatgag gatgaaaatc tctgtcctct gcatcacgca    240
gcagcagaag gtcaagttga actgatgaa ctgatcatca atggttcttc gtgtgaagtg    300
ctgaatataa tggatggtta tggaaatacc ccactgcatt gtgctgcaga aaaaaatcaa    360
gttgaaagtg taaagtttct tctcagccaa ggagcaaatc caaacctccg aaatagaaac    420
atgatgtcac cccttcacat agctgtgcat ggcatgtaca acgaagtgat caaggtgttg    480
actgagcaca aggccactaa catcaattta gaaggagaga tgggaacac ggctttgatg    540 tccacgtgtg ccaaagacaa cagtgaagct ttgcaaattt tgttagaaaa aggagctaag    600
ctgtgtaaat caaataagtg gggagactac cctgtgcacc aggcagcatt ttcaggtgcc    660
aaaaaatgca tggaattaat cttagcatat ggtgaaaaga acggctacag cagggagact    720
cacattaatt ttgtgaatca caagaaagcc agccctctcc acctagcagt tcaaagcgga    780
gacttggaca tgattaagat gtgcctggac aacggtgcac acatcgacat gatggagaat    840
gccaaatgca tggccctcca ttttgctgca acccagggag ccactgacat cgttaagctc    900
atgatctcat cctataccgg aagtagtgat attgtgaatg cagttgatgg caatcaggag    960
```

```
accctgcttc acagagcctc gttatttgat caccatgacc tggcagaata cctaatatca   1020
gtgggagcag acatcaacag cactgattct gaaggacgct ctccacttat tttagcaaca   1080
gcttctgcat cctggaacat tgtgaatttg ctcctctgta aggtgccaa agtagacata    1140
aaagatcatc ttggacgtaa cttttttgcat ttgactgtgc agcagcctta tggactaaga  1200
aatttgcggc ctgagtttat gcagatgcaa cacatcaaag agctggtgat ggatgaagac   1260
aatgacggat gcacacctct ccattatgcc tgtaggcagg gggttcctgt ctctgtaaat   1320
aacctccttg gcttcaatgt gtccattcat agcaaaagta aagataagaa gtcgcccctg   1380
cattttgcag ccagttatgg gcgcatcaat acatgtcaga gacttctgca agacataagt   1440
gatacgaggc ttttgaatga aggggatctc catgggatga cccctctcca cctggcagca   1500
aaaaatgggc atgataaagt cgttcaactc cttctgaaga aagggggcctt atttctcagt  1560
gaccacaatg gctggactgc tttgcatcac gcctccatgg gtgggtacac tcagaccatg   1620
aaggtcattc ttgatactaa cttgaaatgc acagaccgac tagatgaaga agggaacaca   1680
gcactccact ttgcagcacg ggaaggccat gccaaggctg ttgcaatgct ttgagctac    1740
aatgctgaca tcctcctgaa caagaagcaa gcttcctttc tgcatattgc cctgcacaat   1800
aagcgcaagg aagtggttct cacaaccatc agaaataaaa gatgggatga gtgtcttcaa   1860
gttttcactc ataattctcc aagcaatcga tgtccaatca tggagatggt agaataccc   1920
cccgagtgca tgaaagttct tttagatttc tgcatgatac cttccacaga agacaagtcc   1980
tgtcaagact accatattga gtataatttc aagtatctcc aatgcccatt atccatgacc   2040
aaaaaagtag cacctaccca ggatgtggta tatgagcctc ttacaatcct caatgtcatg   2100
gtccaacata accgcataga actcctcaac caccctgtgt gtagggagta cttactcatg   2160
aaatggtgtg cctatggatt cagagcccat atgatgaacc taggatctta ttgtcttggt   2220
ctcatacccca tgacccttct tgttgtcaaa atacagcctg gaatggcctt caattctact   2280
ggaataatca atggaactag tagtactcat gaggaaagaa tagacactct gaattcattt   2340
ccaataaaaa tatgtatgat tctagttttt ttatcaagta tatttggata ttgcaaagaa   2400
gtgatccaaa ttttccaaca gaaaaggaat tacttcctgg attacaacaa tgctctggaa   2460
tgggttatct atacaactag tatcatcttc gtgttgccct tgttcctcaa catcccagcg   2520
tatatgcagt ggcaatgtgg agcaatagcg atattcttct actggatgaa cttcctactg   2580
tatcttcaaa ggtttgagaa ctgtggaatt ttcattgtta tgttggaggt gattttttaaa  2640
acattgctga gatcgaccgg agtgtttatc ttcctcctac tggcttttgg cctcagcttt   2700
tatgttctcc tgaatttcca agatgccttc agcaccccat tgctttcctt aatccagaca   2760
ttcagtatga tgctaggaga catcaattat cgagatgcct tcctagaacc attgtttaga   2820
aatgagttgg catacccagt cctgacctt tggcagctta ttgccttcac aatgtttgtc    2880
ccaattgttc tcatgaactt actgattggc ttggcggttg gggacattgc tgaggtccag   2940
aagcatgcgt cattgaagag gattgctatg caggtggaac ttcataccaa cttagaaaaa   3000
aagctgccac tctggtactt acgcaaagtg gatcagaggt ccaccatcgt gtatccaaat   3060
agacccaggc acggcaggat gctacggttt tttcattact ttcttaatat gcaagaaaca   3120
cgacaagaag taccaaacat tgacacatgc ttggaaatgg aaatattgaa acagaaatat   3180
cggctgaagg acctcacttc cctcttggaa aagcagcatg agctcatcaa actcatcatc   3240
cagaagatgg agatcatctc agagacagaa gatgaagata accattgctc tttccaagac   3300
```

```
aggttcaaga aggagaggct ggaacagatg cacagcaagt ggaattttgt cttaaacgca    3360
gttaagacta aaacacattg ttctattagc cacccggact tttagttctg tgtcttatgg    3420
gagtgggaga ctgctttaca tacttatttc agtgaatttc agtttggaaa agagcaaaga    3480
aacagaaagt tgactaacat tgctgcatgg agatcctagt tcctgcaacc tcacccatac    3540
atatgctcat atttcctgtc aattactatg tattgagaag atcctttctg acatgttcaa    3600
tttgaacatg aaggatagtc tctttcgagt gaataaaaac cagggttgtt ggaatgcata    3660
ttatggagga taagaattaa tgtaactatt aaggcagaac acaactacat aatacaagat    3720
gcatataatt ccaagtatta tatttaatct cctaccatgt taaaccttcc tgtgttataa    3780
cctgtctggg acactataat ctctgttcct actatgatta gatcatagtc tcaccctcct    3840
cgtcccatca cacatgacat cattttgagc cacatgacag aagtcctagt tagtagactg    3900
tgataagtat gaatgttaca atagaaatgt gttcccttag tgttcatcag ttgtgatggt    3960
ttaaatgaga aacgttgccc acagactcat acatttaaac ccttagtccc agttgttgct    4020
gctgcttagg ggggccacac agccttgctt gctctctcct ttctgagtgt ggagagaaat    4080
gtgatcagta agactcctgc tcctgctgcc atgctcttta ttccattatg gacttcttct    4140
gaaactgcaa gcagaaattc actgttcctt cctcaaattt cttttggtca tggtattata    4200
tcatagcaac agaaactaac ttatgtacca atggtcttaa taaagaataa agcctgtaca    4260
gtc                                                                  4263
```

COMPOUND CONTAINING FARNESYL DIPHOSPHATE FOR MODULATING TRPV3 FUNCTION AND USE THEREOF

CROSS-REFERENCE TO RELATED APPLICATIONS

This application claims priority under 35 USC 119 (a)-(d) to Korea Application No. 10-2008-0121093 filed on Dec. 2, 2008, the contents of which are hereby incorporated by reference in their entirety.

BACKGROUND OF THE INVENTION

The present invention relates to a method for activation of TRPV3 (transient receptor potential vanilloid 3), more precisely a novel use of FPP (farnesyl diphosphate) accelerating TRPV3 activation.

TRPV3 (transient receptor potential vanilloid 3), was first found in 2003 owing to the studies in the fields of human physiology and pharmacology. TRPV3 was presumed to play an essential role in maintaining survival system in various tissues. In particular, TRPV3 is expressed in skin cells and peripheral sensory nerve cells which recognize foreign stimuli. TRPV3 belongs to thermoTRP family (temperature-sensitive transient receptor potential ion channels) that is the pain receptor family recognizing temperature and painful stimuli. It is expected that temperature sensing mechanism of human can be explained by disclosing the functions of TRPV3, the pain receptor, and skin disease can be reduced by the development of a TRPV3 activity regulator. To examine TRPV3 functions and develop a TRPV3 regulator, a TRPV3 specific activator that only works for TRPV3 without affecting any other TRP receptors is required.

To understand basic techniques used for the development of a TRPV3 specific inhibitor, it is important to understand the characteristics of TRPV3. TRPV3 is an ion channel and its activation makes cations migrate into sensory neurons or skin cells, stimulating intracellular signal transduction system. For skin, this calcium signal transduction system regulates cell growth and differentiation and at last determines skin cell destiny. One of the techniques to measure TRPV3 activation is patch-clamp electrophysiological technique measuring the changes of membrane currents after amplifying thereof. And another technique to measure TRPV3 activation is to measure intracellular calcium level based on the fact that TRPV3 is involved in the migration of cations such as calcium ions. The first technique is superior in sensitivity to the second one, but the second technique is superior in high speed to the first one, so that they are complementary to each other. Such techniques to measure TRPV3 activation can be executed by the support of cell line culture technique, TRPV3 DNA control and transfection techniques. Various TRPV3 specific activator candidates are administered to TRPV3 over-expressing cells and then TRPV3 activation therein is measured to select a proper TRPV3 activator and determine its capacity.

A TRPV3 specific activator is an essential element to measure TRPV3 activation for further development of a TRPV3 regulator. However, no reports have been made so far in relation to a TRPV3 specific activator. The known TRPV3 activators so far are camphor, menthol and 2-APB (2-aminoethoxydiphenyl borate). But, 2-APB is not specific to TRPV3 and in fact it can activate other TRP receptors such as TRPV1 and TRPV2, etc, or inactivate IP3 (inositol triphosphate) receptor, suggesting that it is not very useful. Camphor and menthol can activate TRPV3 at high concentration and also activate TRPV1 or TRPM8, suggesting that they are not specific to TRPV3, either.

Wound is healed by the increase of skin cell migration and growth. So, when skin cell migration and growth is inhibited, skin disease caused by over-growth of cells such as psoriasis, lichen planus, keratosis, basal cell carcinoma, hypersensitive dermatitis, atopic dermatitis, seborrheic dermatitis, and keloid can be treated [Pani B & Singh B B, Cell Mol Life Sci. 65(2):205-211, 2008 (keloid, hypersensitive dermatitis, hereditary dermatitis, etc); Hanifin J M, J Invest Dermatol. 2008 (atopy, seborrheic dermatitis); Zhao Y et al., J Invest Dermatol. 128(9):2190-2197, 2008 (atopy, psoriasis); Bovenschen H J et al., Br J Dermatol. 153(1):72-78, 2005 (atopy, lichen planus); Brennan D et al., J Cell Sci. 120 (Pt 5):758-771, 2007 (basal cell carcinoma, keratosis); Bhoumik A et al., Proc Natl Acad Sci USA. 105(5):1674-1679, 2008 (basal cell carcinoma); Teh M T et al., J Cell Sci. 120 (Pt 2):330-339, 2007 (basal cell carcinoma); Birnbaum R Y et al., Nat Genet. 38(7):749-751, 2006 (keratosis, lichen planus); Lim C P et al., Oncogene. 25(39):5416-5425, 2006 (keloid); Lim C P et al., J Invest Dermatol. 2008 (keloid); Korean Patent No 10-0771523 (psoriasis, hypersensitive dermatitis, lichen planus, basal cell carcinoma)]. For example, calcipotriol (product name: DAIVONEX) inhibits proliferation of keratinocytes, the myoblasts of HaCat skin cells, so that it is believed to have treatment effect on the propagative skin disease such as psoriasis. In fact, it has been sold as a drug for psoriasis treatment.

The present inventors constructed cell lines expressing different TRPs and investigated their responses to FPP (farnesyl diphosphate) and other chemicals known as TRP regulators. As a result, the present inventors completed this invention by confirming that FPP activated TRPV3 specifically, so that it could be effectively used for the screening of a TRPV3 activity inhibitor, and FPP also inhibited migration and proliferation of skin cells, so that it could be effectively used for treating skin disease caused by wound healing and over-proliferation of skin cells.

SUMMARY OF THE INVENTION

It is an object of the present invention to provide a method for activation of TRPV3 (transient receptor potential vanilloid 3) using FPP (farnesyl diphosphate; 3,7,11-trimethyl-dodeca-2,6,10-trien-1-yl trihydrogen diphosphate).

It is another object of the present invention to provide a method for screening a TRPV3 activity inhibitor using FPP and TRPV3 transformant.

It is further an object of the present invention to provide a method for treating skin disease containing the step of administering a pharmaceutically effective dose of FPP to a subject.

To achieve the above objects, the present invention provides a method for activation of TRPV3 (transient receptor potential vanilloid 3) using FPP (farnesyl diphosphate).

The present invention also provides a method for screening a TRPV3 activity inhibitor comprising the following steps;

1) constructing a transformant by transfecting a host cell with a plasmid harboring the polynucleotide encoding TRPV3;

2) treating the transformant with FPP alone (positive control), and treating the transformant with FPP and TRPV3 activity inhibitor candidates (experimental group);

3) measuring TRPV3 activities in the experimental group and in the control group of step 2); and 4) selecting TRPV3 activity inhibitor candidates that demonstrate significant inhibitory effect compared with the positive control.

The present invention also provides a method for treating skin disease containing the step of administering a pharmaceutically effective dose of FPP to a subject.

FPP of the present invention works specifically on TRPV3, so that it can be effectively used for the study on TRPV3 mechanisms and functions and for the development of a TRPV3 based pain killer.

BRIEF DESCRIPTION OF THE DRAWINGS

The application of the preferred embodiments of the present invention is best understood with reference to the accompanying drawings, wherein.

a: fast increase of whole cell current at +60 mV and −60 mV (n=59) in TRPV3-transfected HEK293T cells treated with 1 µM of FPP; and b: Increase of calcium level in mTRPA3 transformant cells over FPP concentration.

Figure 2:
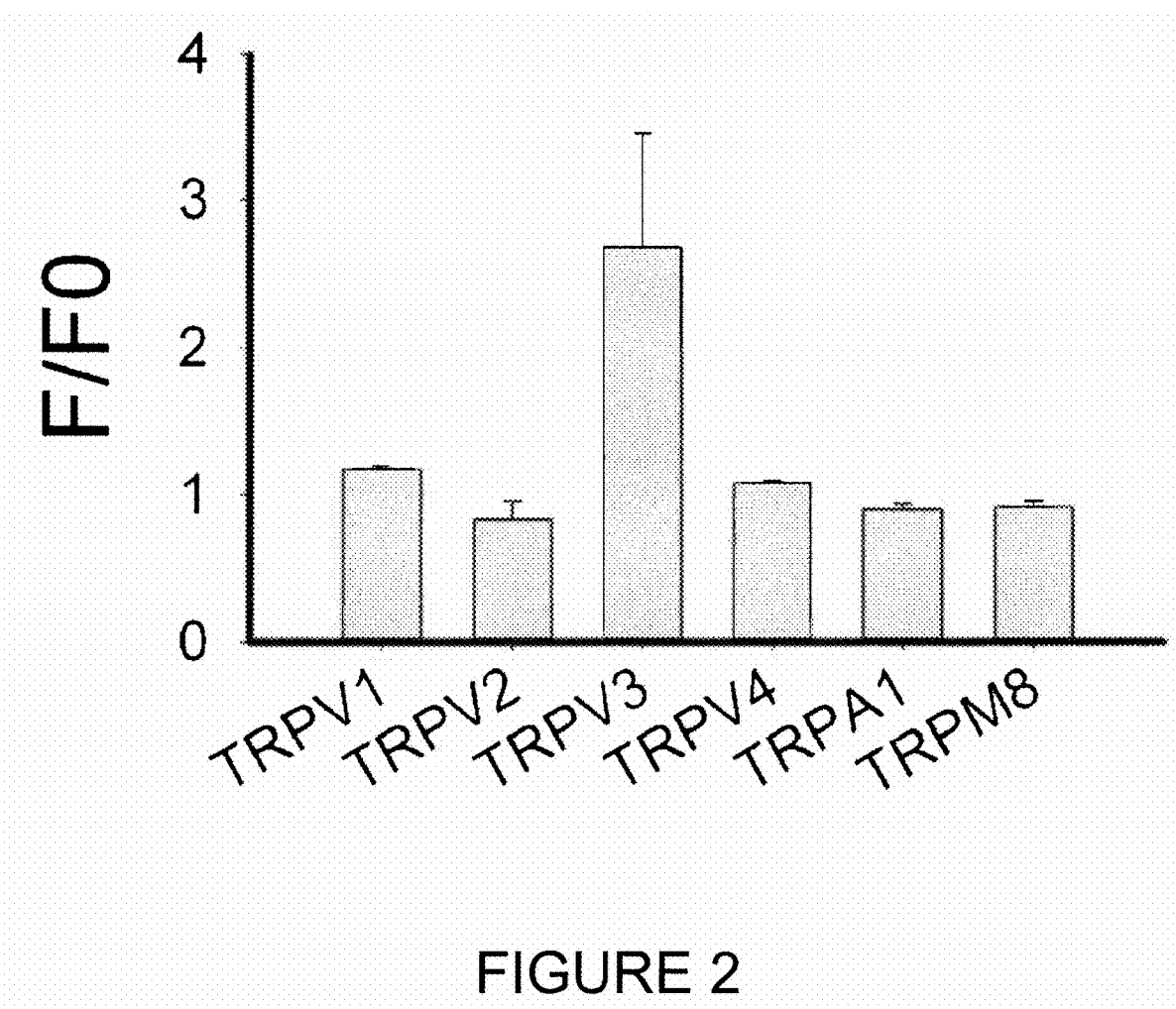

FIG. 2 is a diagram illustrating the FPP reactivity in different transformant cells.

Figure 3:
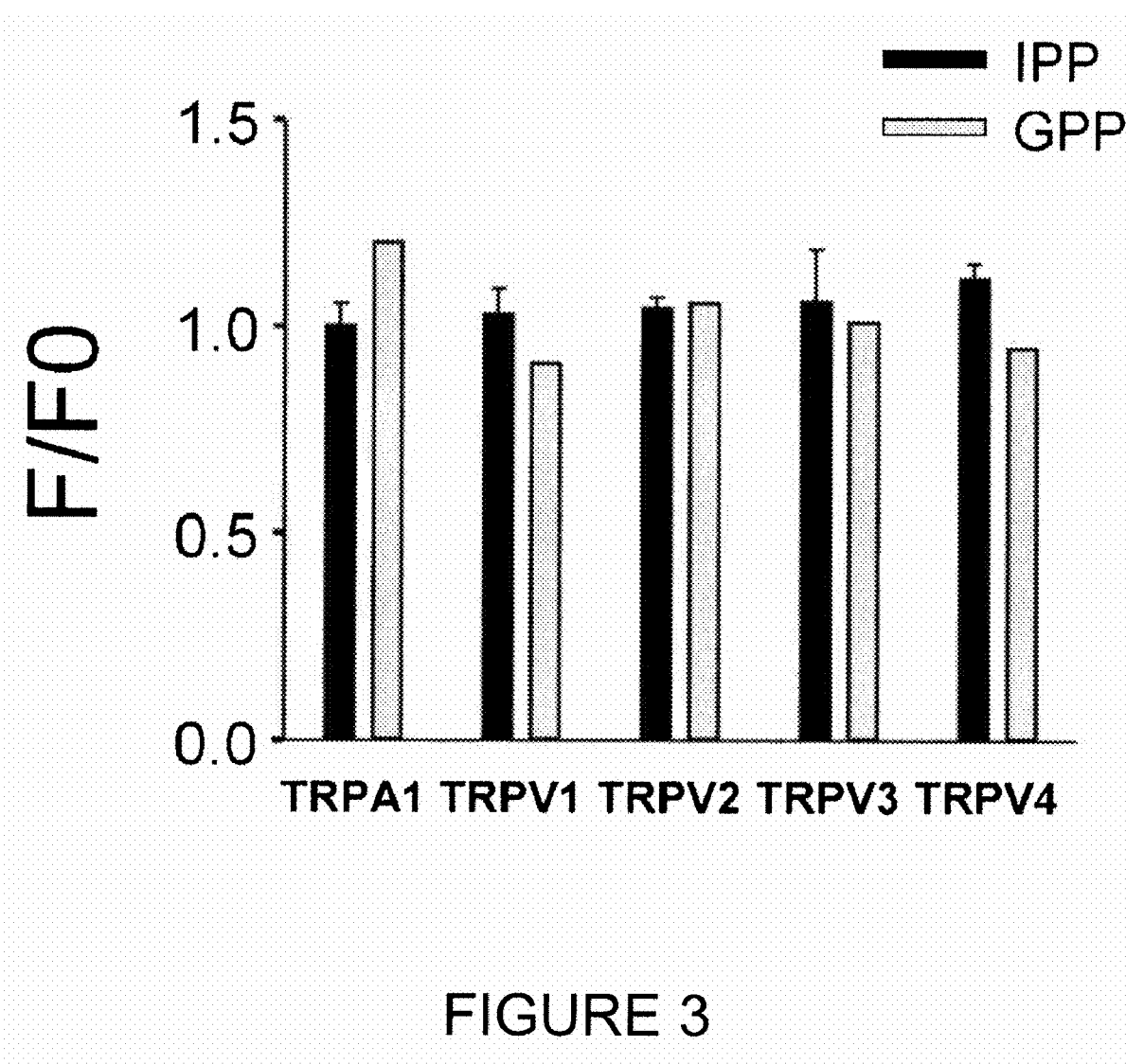

FIG. 3 is a diagram illustrating that FPP analogues, IPP and GPP, do not induce any activity in different transformant cells.

Figure 4:
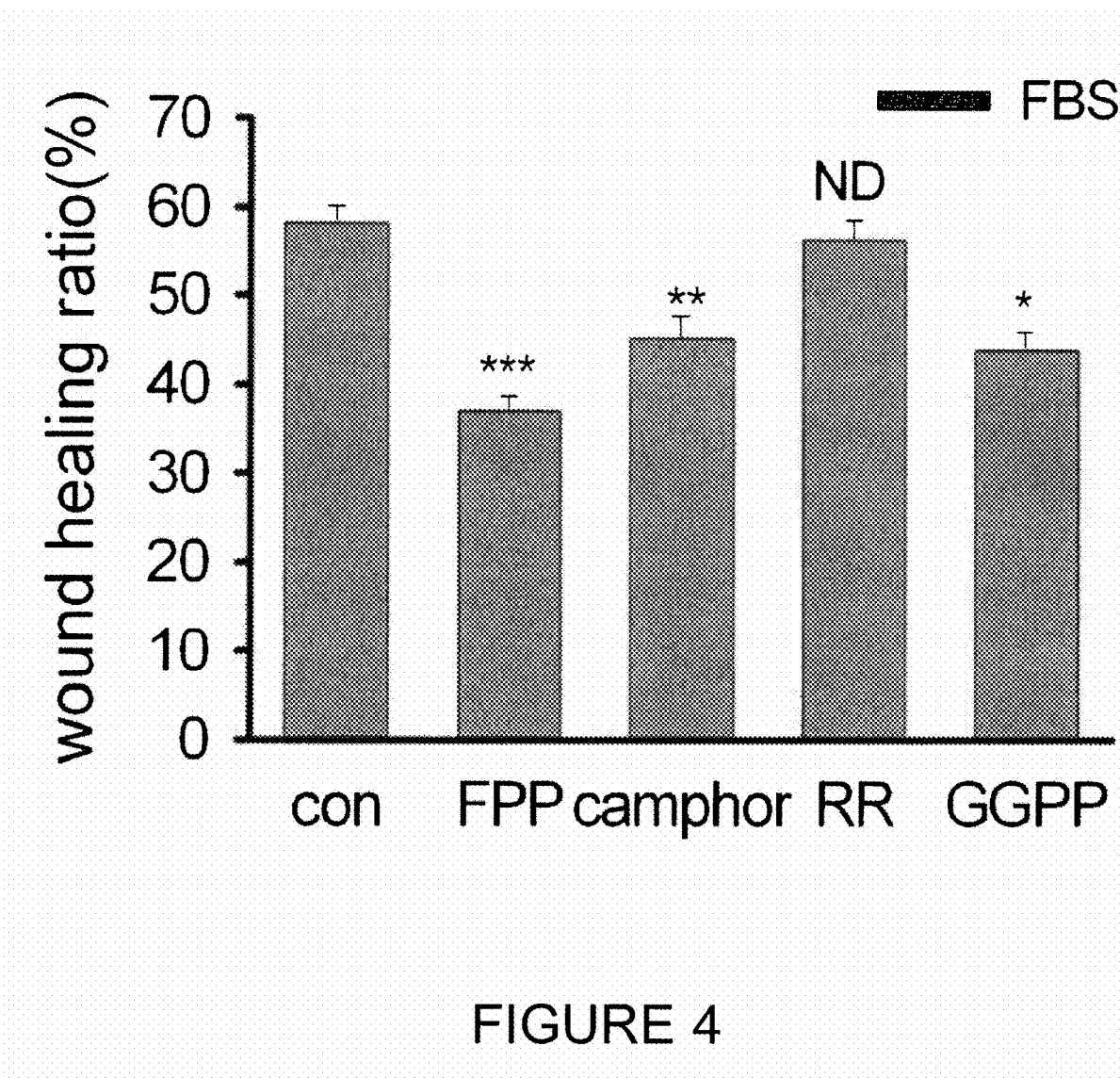

FIG. 4 is a diagram illustrating the inhibition of migration and proliferation of cells by FPP.

Figure 5A:
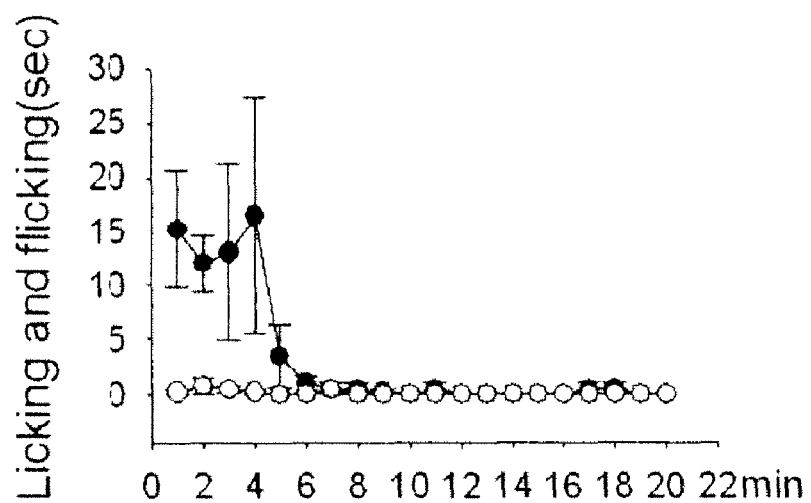

FIG. 5 is a diagram illustrating that pain is induced by FPP under inflammatory condition.

a: 300 µM of FPP and 20 µl of CFA b: histogram illustrating the results of 20-minute reaction in FIG. 5a. (The time required was statistically calculated by T-test, for which CFA alone was regarded as standard).

DETAILED DESCRIPTION OF THE INVENTION

Hereinafter, the present invention is described in detail.

The present invention provides a method for activation of TRPV3 containing the step of contacting FPP (farnesyl diphosphate) with the transformant transfected with a plasmid harboring the polynucleotide encoding TRPV3.

FPP plays a role in accelerating TRPV3 activation. In a preferred embodiment of the present invention, whole cell voltage clamp experiment, a kind of patch clamp techniques, and calcium imaging, a technique to detect intracellular calcium level changes, were performed to investigate the effect of camphor known as a TRPV3 activator and FPP on TRPV3. As a result, TRPV3 activity was significantly increased as soon as FPP was treated. But, the activity was not so much increased when camphor was treated even with higher dose (4 mM) than FPP (1 µM) (see FIG. 1a). The activity was inhibited by ruthenium red which is the general TRP pore blocker (see FIG. 1a).

FPP activates TRPV3 at a low concentration. In a preferred embodiment of the present invention, TRPV3 transformant cells were treated with FPP at different concentrations. $EC_{50}$ (effective concentration 50%) of FPP to TRPV3 was 31.9 nM and maximal effective dose was approximately 1 µM (see FIG. 1a). This result indicates that the TRPV3 regulator can activate TRPV3 at nano-molar concentration range.

FPP activates TRPV3 specifically. In a preferred embodiment of the present invention, FPP activity was investigated in transformant cell lines expressing TRPA1 (transient receptor potential cation channel, subfamily A, member 1), TRPV1, TRPV2, TRPV4 and TRPM8 (transient receptor potential cation channel, subfamily M, member 8) among TRPs known to be expressed in sensory neurons. As a result, FPP did not exhibited activity in those cell lines (see FIG. 2). That is, FPP had TRPV3 specific activity. In a preferred embodiment of the present invention, It was additionally confirmed that FPP analogues IPP (isopentenyl pyrophosphate) and GPP (geranyl pyrophosphate) did not exhibit activity to any TRP channel known to be expressed in sensory neurons (see FIG. 3).

FPP demonstrated TRPV3 specific activity. So, it can be effectively used for separating TRPV3 positive cells from sensory neurons or skin cells. Particularly, FPP facilitates understanding of pain recognition mechanism of sensory neurons or skin cell (ex: sensitivity to heat, chemical and mechanical stimuli) and diagnosis of such disease as inflammatory pain, neuropathic pain and pain by adverse drug reaction. Once FPP is administered to an animal, pain response is measured to judge whether TRPV3 activation affects real behavior response, by which it can be judged which pain response is related to TRPV3. Besides, FPP is also effective in development of a TRPV3 activity inhibitor. FPP can be used as a standard material for the selection of TRPV3 activator candidates. FPP can also be used to determine whether a TRPV3 activity inhibitor candidate inhibits TRPV3 activity induced by FPP. In addition, FPP induces activity at a very low concentration, so that it can be changed by chemical process to be an activator or activity inhibitor with higher strength.

FPP of the present invention can be formulated for oral administration, for example powders, granules, tablets, capsules, suspensions, emulsions, and syrups, and for parenteral administration, for example external use, suppositories and sterile injections, etc.

Solid formulations for oral administration are powders, granules, tablets, capsules, soft capsules and pills. Liquid formulations for oral administration are suspensions, solutions, emulsions and syrups, and the above-mentioned formulations can contain various excipients such as wetting agents, sweeteners, aromatics and preservatives in addition to generally used simple diluents such as water and liquid paraffin. For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The present invention also provides a method for screening a TRPV3 activity inhibitor comprising the following steps:

1) constructing a transformant by transfecting a host cell with a plasmid harboring the polynucleotide encoding TRPV3;

2) treating the transformant with FPP alone (positive control), and treating the transformant with FPP and TRPV3 activity inhibitor candidates (experimental group);

3) measuring TRPV3 ion channel activities in the experimental group and in the control group of step 2); and 4) selecting TRPV3 activity inhibitor candidates that demonstrate higher or similar inhibitory effect compared with the positive control.

In a preferred embodiment of the present invention, among TRPs known to be expressed in sensory neurons or skin cells, TRPV3 was specifically activated by FPP (see FIG. 2). So, the said FPP can be effectively used for the screening of a TRPV3 activity inhibitor.

The host cell herein is preferably any cell line that can be used for the study of calcium channel activity and high throughput screening of an inhibitor, for example HEK, CHO, HeLa, RBL-2H3, and HaCat, but not always limited thereto.

The candidate of step 1) is preferably natural compounds, synthetic compounds, RNA, DNA, polypeptides, enzymes, proteins, ligands, antibodies, antigens, bacterial or fungal metabolites or biological molecules, but not always limited thereto.

FPP of step 2) activates TRPV3 specifically. It has already been known that 2-APB, camphor and menthol activate TRPV3. However, they are not TRPV3 specific. That is, 2-APB activates not only TRPA1 but also TRPV1 and TRPV2. Camphor activates TRPV1 also and menthol activates TRPM8 and TRPA1 as well.

The measuring of ion channel activity of step 3) can be performed by whole cell voltage clamp technique or calcium imaging.

The preferable concentration of FPP is 10-1000 nM. In a preferred embodiment of the present invention, $EC_{50}$ (effective concentration 50%) of FPP to TRPV3 was 31.9 nM and maximal effective dose was approximately 1 μM. This result indicates that FPP can activate TRPV3 at nano-molar concentration range (see FIG. 1b).

The present invention also provides a method for treating skin disease containing the step of administering a pharmaceutically effective dose of FPP to a subject.

In a preferred embodiment of the present invention, it was confirmed that FPP inhibited HaCat skin cell migration and proliferation (see FIG. 4). Therefore, FPP can be effectively used for the treatment of skin disease induced by wound healing and over-proliferation of cells.

The skin disease herein is resulted from wound healing and over-proliferation of cells, which is selected from the group consisting of psoriasis, lichen planus, keratosis, basal cell carcinoma, hypersensitive dermatitis, atopic dermatitis, seborrheic dermatitis, and keloid.

The subject herein is one of vertebrates and preferably mammals and more preferably selected from such test animals as rats, rabbits, guinea pigs, hamsters, dogs and cats, and most preferably apes such as chimpanzees and gorillas. FPP of the present invention can be administered orally or parenterally. For example the possible administration pathway can be oral administration, rectal administration, intravenous injection, intramuscular injection, hypodermic injection, intrauterine injection or intracerebroventricular injection. The composition for inhibiting pain of the present invention can be administered alone or treated together with surgical operation, hormone therapy, chemo-therapy and biological regulators.

The effective dosage of the pharmaceutical composition of the present invention can be determined by those in the art according to condition and weight of a patient, severity of a disease, type of a drug, administration pathway and duration. Preferably, the composition of the present invention can be administered by 0.0001-100 mg/kg per day, and more preferably by 0.001-100 mg/kg per day. The administration frequency is once a day or a few times a day.

FPP of the present invention can be provided as a pharmaceutical composition. The composition can include, in addition to FPP, one or more effective ingredients having the same or similar function to FPP. The pharmaceutical composition of the present invention preferably includes FPP by 0.0001-10 weight % and more preferably 0.001-1 weight % for the total weight of the composition.

The pharmaceutical composition of the present invention can additionally include generally used carriers, excipients, disintegrating agents, sweetening agents, lubricants, flavors and diluents. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. The disintegrating agent is exemplified by sodium carboxy methyl starch, crospovidone, croscarmellose sodium, alginic acid, calcium carboxymethyl cellulose, sodium carboxymethyl cellulose, chitosan, guar gum, low-substituted hydroxypropyl cellulose, magnesium aluminum silicate, polacrilin potassium, etc.

The pharmaceutical composition of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1-90 weight part to the pharmaceutical composition.

The composition of the present invention can be administered orally or parenterally. For example the possible administration pathway can be oral administration, external application, intraperitoneal injection, rectal administration, hypodermic injection, intravenous injection, intramuscular injection, or intrathoracic injection.

In addition, FPP of the present invention can be provided in the form of functional food.

In a preferred embodiment of the present invention, it was confirmed that FPP inhibited HaCat skin cell migration and proliferation (see FIG. 4). Therefore, FPP can be effectively used for the treatment of skin disease induced by wound healing and over-proliferation of cells.

The skin disease herein is resulted from wound healing and over-proliferation of cells, which is selected from the group consisting of psoriasis, lichen planus, keratosis, basal cell carcinoma, hypersensitive dermatitis, atopic dermatitis, seborrheic dermatitis, and keloid.

FPP of the present invention can be used as food additive. In that case, FPP can be added as it is or as mixed with other food components according to the conventional method. The mixing ratio of active ingredients can be regulated according to the purpose of use (prevention or health enhancement). In general, to produce health food or beverages, FPP is added preferably by 0.2-20 weight % and more preferably by 0.24-10 weight %. However, if long term administration is required for health and hygiene or regulating health condition, the content can be lower than the above but higher content can be accepted as well since FPP has been proved to be very safe.

The health food of the present invention can additionally include various flavors or natural carbohydrates, etc. like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 weight part and more preferably 0.02-0.03 weight part in 100 weight part of the health food of the present invention.

The food herein is not limited. For example, isopentenyl pyrophosphate of the present invention can be added to meat, sausages, bread, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

In addition to the ingredients mentioned above, the health food of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The health food of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 001-0.1 weight part per 100 weight part of the health food of the present invention.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Construction of Cell Lines Transfected with TRPV

HEK293T cell line (ATCC CRL-11268) was transiently transfected with plasmid DNA containing polynucleotide encoding rTRPA1 (SEQ. ID. NO: 1), rTRPV2 (SEQ. ID. NO: 2), mTRPV3 (SEQ. ID. NO: 3), rTRPV4 (SEQ. ID. NO: 4), mTRPM8 (SEQ. ID. NO: 5) or mTRPA1 (SEQ. ID. NO: 6).

Particularly, the HEK293T cell line was transiently transfected with 3 μg/35 mm dish of rTRPV1, rTRPV2, mTRPV3, rTRPV4, mTRPM8 and mTRPA1 plasmid DNA, and 600 ng/well of pCDNA3 (Invitrogen Corp., USA; containing green fluorescent protein (GFP) cDNA) using Fugene6 (Roche Diagnostics, USA) according to manufacturer's instruction. The transformed cells were cultured in DMEM/F12 medium containing 10% FBS and 1% penicillin/streptomycin in a $CO_2$ incubator for 24 hours. The cells were smeared on poly-L-lysine-coated glass coverslips, followed by further culture for 10-24 hours.

Example 2

Investigation of TRPV3 Activation by FPP

<2-1> Treatment of FPP and Camphor

Figure 1A:
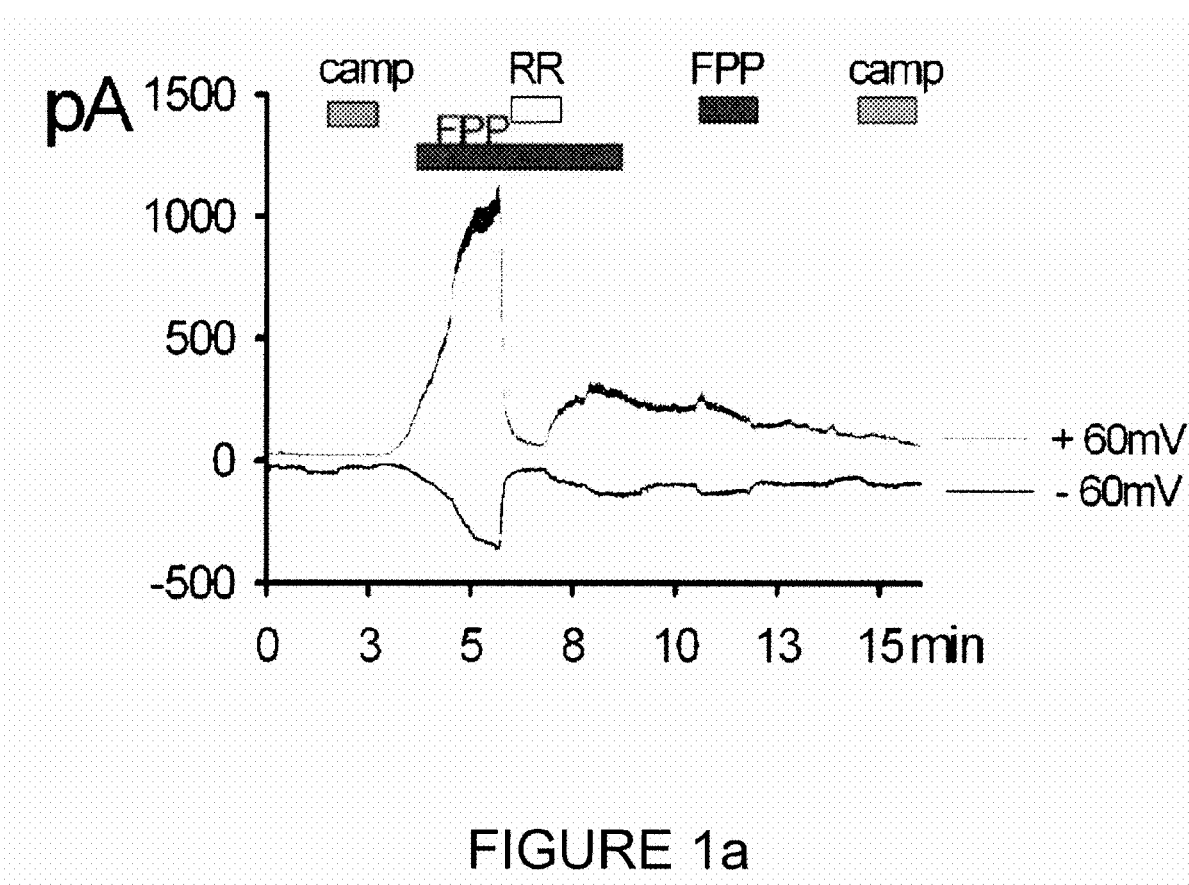
FIG. 1 is a diagram illustrating the TRPV3 activity induced by FPP (Camp: camphor, RR: ruthenium red)

The mTRPV3 transfected cell line prepared in Example 1 was treated with 1 μM of FPP (Biomol, USA), 4 mM of camphor (Sigma-Aldrich, USA) and ruthenium red (RR; Sigma-Aldrich, USA) at a required time intervals as shown in FIG. 1a. Stock solutions were made using water or DMSO, and were diluted with test solutions before use.

<2-2> Whole Cell Voltage Clamp Experiment

Whole-cell voltage-clamp recording, one of the patch-clamp techniques, was performed with the transfected cell line of Example <1-1> according to the method of Bandel M, et al. (Neuron 41:849-857, 2004).

Particularly, the extracellular solution (140 mM NaCl, 5 mM KCl, 2 mM $CaCl_2$, 1 mM $MgCl_2$, 10 mM HEPES; titrated to pH 7.4 with NaOH) and the pipette solution (140 mM CsCl, 5 mM EGTA, 10 mM HEPES, 2.0 mM MgATP, 0.2 mM NaGTP; titrated to pH 7.2 with CSOH) were used. The potential was held at −60 mV for 250 ms, voltage-ramp pulsed from −80 mV to +80 mV for 325 seconds and returned to −60 mV for 250 ms, which was repeated without inter-sweep. This experiment was repeated 5 times.

As a result, as shown in FIG. 1a, as soon as FPP was treated, significant increase of TRPV3 activity was observed (Fluo-3 calcium imaging, n=59). However, when camphor (4 mM) known as a TRPV3 activator was treated, the activity was not so much increased even at a higher concentration than FPP (1 μM). The activity was reduced by ruthenium red known as a general TRP ion channel blocker.

Experimental Example 3

FPP Specific and Dose-Dependent Response of TRPV3

<3-1> Treatment of FPP at Different Concentrations

The mTRPV3 transfected cell line prepared in Example 1 was treated with FPP at different concentrations from 0.1 to 1,000 nM.

<3-2> Measurement of Intracellular Calcium Level Changes by Calcium Imaging

Calcium imaging was performed with the transfected cell line treated as above.

Particularly, the transfected cell line of Example <3-1> was loaded with Fluo-3AM (5 μM; Sigma Aldrich, USA) in the bath solution (140 mM NaCl, 5 mM KCl, 2 mM $CaCl_2$, 1 mM $MgCl_2$, 10 mM HEPES; adjusted to pH 7.4 with NaOH) containing 0.02% pluronic acid (Invitrogen, USA) at 37° C. for 1 hour. Calcium imaging was performed with LSM5 Pascal confocal microscope (Carl Zeiss, Germany), and time-lapse images (excitation 488 nm/emission 514 nm) were collected every 3 seconds using Carl Zeiss ratio tool software (Carl Zeiss, Germany). Mean value curve of calcium influx response (n=12–62 per each experimental values) was made by Hill plot.

Figure 1B:
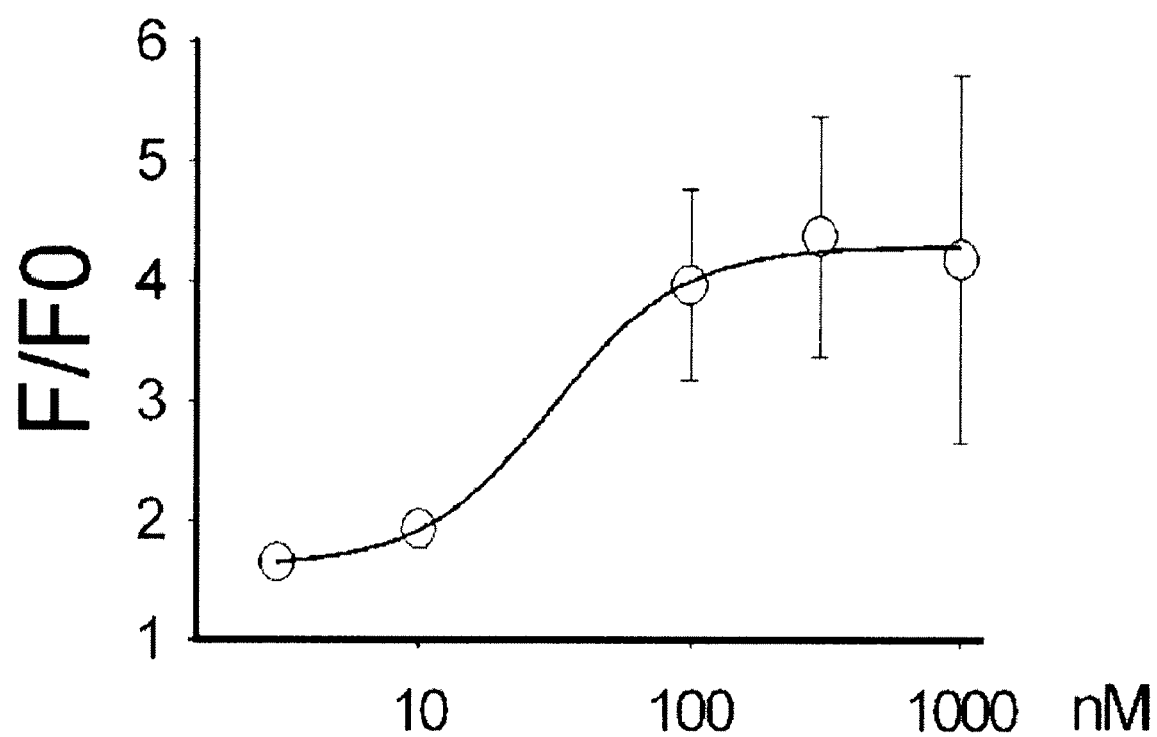

As shown in FIG. 1b, $EC_{50}$ (effective concentration 50%) of FPP to TRPV3 was 31.9 nM and maximal effective dose was approximately 1 μM (see FIG. 1a). This result indicates that the TRPV3 regulator can activate TRPV3 at nano-molar concentration range.

Example 4

Investigation of Responses to FPP in Different TRP Transfected Cell Lines

The TRPA1, TRPV1, TRPV2, TRPV3, TRPV4 and TRPM8 transfected cell lines prepared by the method of Example 1 and the non-transfected HEK cell line (control group) were treated with 1 μM of FPP. Calcium imaging was performed with the transfected cell lines treated as the above by the same manner as described in Example <3-2>.

As a result, as shown in FIG. 2, among 5 TRPs known to be expressed in sensory neurons or skin cells, only TRPV3 was activated by FPP.

Example 5

Investigation of Responses to TRPV3 Regulator Analogues

The TRPA1, TRPV1, TRPV2, TRPV3, TRPV4 and TRPM8 transfected cell lines prepared by the method of Example 1 and the non-transfected HEK cell line (control group) were treated with 10 μM of IPP (isopentenyl pyrophosphate: Biomol, USA) and 10 μM of GGPP (geranylgeranyl pyrophosphate: Biomol, USA), the TRPV3 regulator analogues. Calcium imaging was performed with the transfected cell lines treated as the above by the same manner as described in Example <3-2>.

As a result, as shown in FIG. 3, any of 5 TRP channels known to be expressed in sensory neurons or skin cells was not activated. Therefore, it was confirmed that only FPP could activate TRPV3 specifically and its analogues such as IPP or GGPP did not induce TRPV3 activation.

Example 6

Inhibition of Cell Migration and Proliferation by FPP

HaCat (ATCC, CCL-228) cell line was seeded in a 24-well plate. The present inventors drew lines 1 mm deep on the well fully filled with the cells to make artificial wound. The wounded cells were treated with FPP (1 μM), camphor (4 mM), RR (20 μM) and GGPP (10 μM) respectively and incubated in a $CO_2$ incubator for 12 hours. The control group was not-treated. The width of recovered wound was measured under microscope and compared with that at the beginning, which was presented as wound recovery rate. All the experiments were performed on DMEM/FBS. Floating cells, which means dead cells, after making wound, were eliminated by using PBS to eliminate variables caused by dead cells. The cells were observed under microscope (×40, IX 71 OLYMPUS), and distance was measured by using image analysis program (Meta-flour 7.1, Molecular Devices, USA).

As shown in FIG. 4, migration and proliferation of HaCat skin cells administered with 1 μM of FPP were investigated 12 hours after the treatment. As a result, migration and proliferation of the HaCat skin cells were significantly inhibited by FPP and the inhibitory effect was most significant compared with those of other drugs.

Example 7

Investigation of Pain Inducing Activity of FPP by Animal Test

<7-1> Inducement of Inflammatory Sensitization

Inflammatory sensitization by FPP was investigated. Particularly, 10 μl of CFA (complete Freund's adjuvant; Sigma Aldrich, USA) was injected to the right hind paws of mice 24 hours before the FPP injection. Before the experiment, the mice were adapted for one hour to the experimental environment. 10 μl of vehicle (saline containing 3% DMSO and 0.5% Tween 80) alone or 10 μl of vehicle containing FPP (3 mM) was injected to the right hind paws of the mice.

<7-2> Investigation of Acute Licking/Flicking Behaviors

The time spent for the hind paw licking/flicking behaviors in mice were measured according to the method of Bandell M, et al. (Neuron 41:849-857, 2004) and Moqrich A, et al. (Science 307:1468-1472, 2005), for 20 minutes.

Control: not-treated;
Experimental group 1.20 μl of CFA+300 μM of FPP PBS solution (black circle);
Experimental group 2.20 μl of CFA (white circle).

Figure 5B:
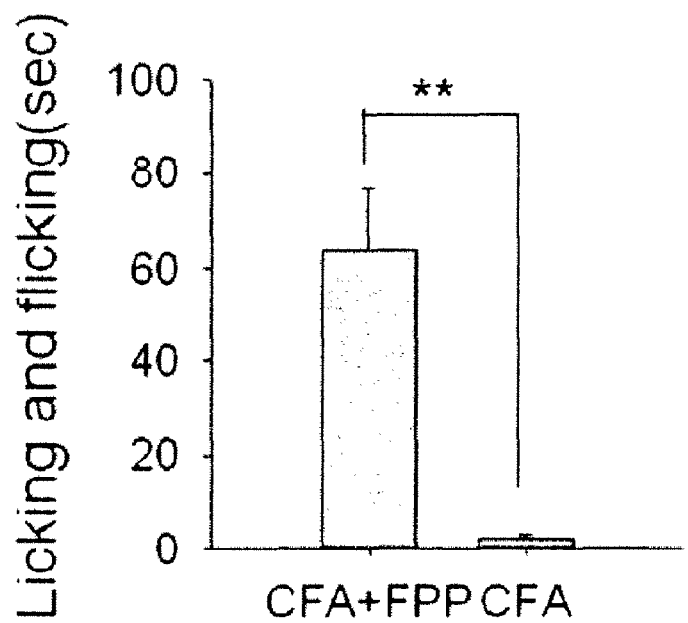

As a result, as shown in FIG. 5, pain was induced by the treatment of FPP under inflammatory condition made by CFA injection (FIG. 5a). The result of 20 minute-reaction induced in animals was also consistent with the result shown in FIG. 5b.

The mice treated with FPP demonstrated significantly increased licking/flicking behavior, compared with the mice not-treated.

The Manufacturing Examples of the composition for the present invention are described hereinafter.

Manufacturing Example 1

Preparation of Pharmaceutical Formulations

<1-1> Preparation of Powders

| | |
|---|---|
| FPP | 2 g |
| Lactose | 1 g |

Powders were prepared by mixing all the above components, which were filled in airtight packs according to the conventional method for preparing powders.

<1-2> Preparation of Tablets

| | |
|---|---|
| FPP | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| FPP | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| FPP | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| FPP | 150 mg |
| Soybean extract | 50 mg |
| Glucose | 200 mg |
| Star | 600 mg |

All the above components were mixed, to which 100 mg of 30% ethanol was added. The mixture was dried at 60° C. and the prepared granules were filled in packs.

Manufacturing Example 2

Preparation of Dairy Products

5~10 weight part of FPP of the present invention was added to milk. Health enhancing dairy products such as butter and ice cream were prepared with the milk mixture according to the conventional method.

Manufacturing Example 3

Preparation of Beverages

| | |
|---|---|
| FPP | 1000 mg |
| Citric acid | 1000 mg |
| Oligosaccharide | 100 g |
| Maesil (*Prunus mume*) Extract | 2 g |
| Taurine | 1 g |
| Purified water | up to 900 Ml |

The above constituents were mixed according to the conventional method for preparing health beverages. The mixture was heated at 85□ for 1 hour with stirring and then filtered. The filtrate was loaded in 2 liter sterilized containers, which were sealed and sterilized again, stored in a refrigerator until they would be used for the preparation of a composition for health beverages. The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for activating TRPV3 (transient receptor potential vanilloid 3) containing the step of contacting FPP (farnesyl diphosphate) with a transformant prepared by transfecting a host cell with a plasmid comprising a polynucleotide encoding TRPV3.

2. The method for activating TRPV3 according to claim 1, wherein the FPP activates TRPV3 specifically.

3. A method for screening one or more TRPV3 activity inhibitor candidates comprising the following steps:
   1) constructing a transformant by transfecting a host cell with a plasmid comprising a polynucleotide encoding TRPV3;
   2) treating the transformant with FPP alone (positive control), and treating the transformant with FPP and TRPV3 activity inhibitor candidates (experimental group);
   3) measuring TRPV3 ion channel activities in the experimental group and in the control group of step 2); and
   4) selecting TRPV3 activity inhibitor candidates that demonstrate an inhibitory effect compared with the positive control.

4. The method for screening one or more TRPV3 activity inhibitor candidates according to claim 3, wherein the FPP is administered at a concentration of 10-1000 μM.

5. The method for screening one or more TRPV3 activity inhibitor candidates according to claim 3, wherein the one or more candidates are selected from the group consisting of natural compounds, synthetic compounds, RNA, DNA, polypeptides, enzymes, proteins, ligands, antibodies, antigens, bacterial or fungal metabolites and biological molecules.

6. The method for screening one or more TRPV3 activity inhibitor candidates according to claim 3, wherein the measurement of TRPV3 activity in step 3) is performed by whole cell voltage clamp technique or calcium imaging.

* * * * *